(12) United States Patent
Van Lue

(10) Patent No.: US 8,137,268 B2
(45) Date of Patent: Mar. 20, 2012

(54) MAGNETIC SURGICAL RETRACTOR

(75) Inventor: Stephen J. Van Lue, Santa Clara, CA (US)

(73) Assignee: Van Lue Veterinary Surgical, LLC, Winter Springs, FL (US)

( * ) Notice: Subject to any disclaimer, the term of this patent is extended or adjusted under 35 U.S.C. 154(b) by 7 days.

(21) Appl. No.: 12/655,628

(22) Filed: Jan. 4, 2010

(65) Prior Publication Data
US 2010/0160739 A1 Jun. 24, 2010

Related U.S. Application Data

(62) Division of application No. 11/321,786, filed on Dec. 29, 2005, now abandoned.

(51) Int. Cl.
*A61B 1/32* (2006.01)
(52) U.S. Cl. ............... 600/227; 600/12; 600/237
(58) Field of Classification Search ........... 606/201–246
See application file for complete search history.

(56) References Cited

U.S. PATENT DOCUMENTS

| | | | |
|---|---|---|---|
| 3,370,901 A | 2/1968 | Andrews | |
| 4,205,678 A * | 6/1980 | Adair | 604/343 |
| 4,592,344 A | 6/1986 | Scheer | |
| 4,809,713 A | 3/1989 | Grayzel | |
| 4,850,963 A | 7/1989 | Sparks et al. | |
| 4,871,310 A | 10/1989 | Vardimon | |
| 4,971,557 A | 11/1990 | Martin | |
| 5,067,952 A | 11/1991 | Gudov et al. | |
| 5,115,799 A | 5/1992 | McGann | |
| 5,302,121 A | 4/1994 | Gagin | |
| 5,593,379 A | 1/1997 | Rayman | |

(Continued)

FOREIGN PATENT DOCUMENTS
WO   WO 2005/002415   1/2005
(Continued)

OTHER PUBLICATIONS
Hirsch, T.R., et al., "The Doctor Will See You Now," Dental Town Magazine., Apr. 2004 pp. 22-24, 26.
(Continued)

*Primary Examiner* — Eduardo C Robert
*Assistant Examiner* — Jerry Cumberledge
(74) *Attorney, Agent, or Firm* — David M. Quinlan, P.C.

(57) ABSTRACT

A method for holding a hollow internal organ in a desired location during a medical procedure uses a retractor device and a gripper element, each of which includes a magnetic member, one being a first magnet and the other being either a second magnet or a non-magnetized magnetically permeable member. The retractor device is placed into the lumen of the organ and the gripper element is located outside the body cavity of the patient. The magnetic members of the gripper element and the retractor device are brought into proximity with each other to capture a wall of the hollow organ and a body wall of the patient between them, with the gripper element being held at a location that secures the organ at the desired location. In another embodiment, the gripper element is placed inside the body cavity of the patient and outside the organ, with the magnetic members of the gripper element and the retractor device in proximity with each other to capture a wall of the hollow organ between them. A portion of a cord, the distal end of which is attached to the gripper element, is located externally of the patient and anchored at a location that secures the organ at the desired location.

24 Claims, 7 Drawing Sheets

U.S. PATENT DOCUMENTS

| | | | |
|---|---|---|---|
| 5,730,597 A | 3/1998 | Luttrell | |
| 6,080,105 A | 6/2000 | Spears | |
| 6,102,701 A | 8/2000 | Engeron | |
| 6,315,709 B1 | 11/2001 | Garibaldi et al. | |
| 6,358,196 B1 | 3/2002 | Rayman | |
| 6,394,802 B1 | 5/2002 | Hahn | |
| 6,471,172 B1 * | 10/2002 | Lemke et al. | 248/278.1 |
| 6,824,511 B1 * | 11/2004 | Bell et al. | 600/227 |
| 7,338,434 B1 * | 3/2008 | Haarstad et al. | 600/37 |
| 7,429,259 B2 | 9/2008 | Cadeddu et al. | |
| 2001/0049497 A1 | 12/2001 | Kalloo et al. | |
| 2002/0082470 A1 | 6/2002 | DeVries et al. | |
| 2002/0151759 A1 | 10/2002 | Paturu | |
| 2003/0095781 A1 | 5/2003 | Williams | |
| 2003/0104339 A1 | 6/2003 | Fromovich | |
| 2003/0114731 A1 | 6/2003 | Cadeddu et al. | |
| 2004/0002665 A1 | 1/2004 | Parihar et al. | |
| 2004/0049102 A1 * | 3/2004 | Nelson et al. | 600/240 |
| 2004/0186356 A1 * | 9/2004 | O'Malley et al. | 600/231 |
| 2005/0059864 A1 * | 3/2005 | Fromovich et al. | 600/201 |
| 2006/0149135 A1 * | 7/2006 | Paz | 600/201 |
| 2006/0161050 A1 * | 7/2006 | Butler et al. | 600/208 |
| 2006/0270899 A1 | 11/2006 | Amirana | |
| 2007/0004958 A1 | 1/2007 | Ohdaira | |
| 2007/0255273 A1 | 11/2007 | Fernandez et al. | |
| 2007/0270629 A1 | 11/2007 | Charles | |
| 2008/0171907 A1 | 7/2008 | Long et al. | |
| 2008/0269779 A1 | 10/2008 | Cadeddu et al. | |
| 2009/0043246 A1 | 2/2009 | Dominguez | |
| 2009/0192344 A1 | 7/2009 | Bakos et al. | |
| 2009/0228028 A1 | 9/2009 | Coe et al. | |

FOREIGN PATENT DOCUMENTS

| | | |
|---|---|---|
| WO | WO 2005/002415 A3 | 1/2005 |
| WO | WO 2006/077200 A1 | 7/2006 |
| WO | WO 2007/130382 A3 | 11/2007 |
| WO | WO 2008/131128 | 10/2008 |

OTHER PUBLICATIONS

Bookwalter Retractor Kit II Codman, copyright, 1997, web page visited Oct. 23, 2005.

Disarp (Disposable Abdominal Retracting Pad), Codan-Produkblad-Disarp, web page visited Oct. 25, 2005.

Freeman, L.J. (ed.) Veterinary Endosurgery, Fig. 8.51, C.V. Mosby, St. Louis, MO (1999).

International Search Report in PCT/US06/49523, Dec. 4, 2007.

Written Opinion of the International Searching Authority in PCT/US06/49523, Dec. 4, 2007.

"Magnetic Marker for Surgery," Technology Abstract—04116, Feb. 14, 2005, pp. 1-2.

* cited by examiner

MAGNETIC SURGICAL RETRACTOR

CROSS-REFERENCE TO RELATED APPLICATION

This application is a division of U.S. application Ser. No. 11/321,786, filed Dec. 29, 2005, now abandoned.

BACKGROUND OF THE INVENTION

1. Field of the Invention

The present invention relates to devices and apparatus for providing access to areas undergoing a surgical/dental procedure, and more particularly, to tissue retractors incorporating magnets.

2. Description of Related Art

There are myriad surgical/dental procedures that require access to hard to reach areas of a patient. One part of the body that has proved particularly challenging in terms of access to target areas undergoing such procedures is the buccal surfaces of the gums and/or teeth in a patient's oral cavity. Increases in both the efficiency and efficacy of these procedures are obtained by providing the dentist or surgeon unfettered access to the area being treated. In addition, surgical procedures on other areas of the body frequently require retraction of tissues not involved in the procedure, or securing tissues in place during the procedure, to expose the area.

The most common approach to providing sufficient space for a dental or surgical procedure is simply to manipulate the tissues not involved and retract them out of the way. For example, a dentist or oral surgeon may engage the edges of a patient's mouth using a manual retractor device that fits over the patient's lips and pulls them back as far as they will stretch. Typical such devices are shown in U.S. Pat. Nos. 4,971,557, 5,115,799, 5,730,597, 6,080,105, and 6,102,701. Such a retractor device may include a contoured surface that fits over the patient's lips and a handle portion for the surgeon, or more commonly, an assistant, to pull manually to retract the patient's lips from the target area. Alternatively, the dentist may use a dental mirror to provide retraction of the buccal tissue while performing the procedure with the contralateral hand. In this manner, the patient's mouth is forcibly expanded and the dentist/surgeon is afforded access to the target area.

This is an imperfect approach because it requires either that the dental practitioner hold the retractor with one hand while performing the procedure with the other, or that an assistant be employed to hold the retractor. The presence of an assistant increases the cost of the procedure to the patient. And even if an assistant is required for other aspects of the procedure, a manual retractor perforce still occupies one of the assistant's hands, thus limiting his or her ability to perform other tasks during the procedure. And using a dental mirror can limit the dentist's visual field because the mirror is first placed as a retractor, and only secondarily as a visual tool.

While these retraction techniques may be acceptable in some circumstances, access to the target area is still limited because the patient's lips can only be distended so far. Moreover, retracting just the lips has a limited effect on moving the buccal surfaces of the cheeks away from the teeth and gums, particularly when the target area is deeper within the patient's oral cavity, such as proximate to the molars. Yet another drawback to using retractors that pull on the patient's lips is that the retractor itself tends to interfere with the procedure because it occupies part of the opening through which the surgeon/dentist accesses the target area. It is also known to use various forms of gauze packing between a patient's buccal surfaces and teeth to provide a degree of access. However, this can severely limit the amount of working space immediately adjacent the target area.

Retraction of tissues in non-dental surgical procedures typically relies on manipulating the uninvolved tissues and moving them out of the way, or packing the tissues and/or organs off (that is, away from the target area) with laparotomy pads, surgical towels, or other similar compliant implements that conform to the shape of the tissues/organs being held in place. Unlike retraction in dental procedures, a surgeon can often enlarge an incision to provide greater access to the target area. But even then, additional manipulation of internal tissues and/or organs is often required to maintain adequate exposure of the target area after access is achieved. For example, in open abdominal surgery, an incision of adequate size can usually be made to provide access, but intra-abdominal tissues and organs (such as the spleen, intestines, etc.) may need to be manipulated to expose the surgical site. This is often accomplished using devices such as Balfour retractors or Bookwalter retractors to hold the wound edges open. These devices incorporate retractor blades of various shapes, and are often used in combination with laparotomy sponges, surgical towels, or other soft, malleable instruments. These devices can decrease the amount of space immediate to the surgical wound, and thus decrease the space for the surgeon to work, but they are necessary to secure the retractor implements and maintain the tissues/organs in a retracted position. In some cases, a sufficient number of laparotomy sponges may be used to maintain the desired position of the tissues without requiring a blade retractor. But the position of the tissues will often change if held in place only by laparotomy sponges, and adjustments will have to be made during the surgery. Moreover, the use of multiple laparotomy sponges is inherently dangerous, since it increases the risk that one or more sponges will remain in the patient after the surgery is completed.

Accordingly, there has been a long-felt need for an improved manner of exposing areas that are targeted for surgical/dental procedures to facilitate the procedures and increase their efficiency and efficacy.

SUMMARY OF THE INVENTION

It is an object of the invention to overcome the disadvantages of the prior art by providing an improved apparatus and method for retracting body tissues during surgical/dental procedures.

In accordance with one aspect of the invention, a magnetic oral retractor assembly for distending the cheek of a patient undergoing an oral dental/surgical procedure comprises a gripper element mounted to a support structure external of the patient's oral cavity and an intraoral retractor device for contacting the inner surface of the patient's cheek, wherein the gripper element and the retractor device each include a magnetic member, at least one of the magnetic members comprising a first magnet, and the other of the magnetic members comprising a second magnet or a non-magnetized magnetically permeable member, the magnetic members being positioned on the gripper element and the retractor device for magnetically coupling the gripper element to the retractor device through the patient's cheek.

In a more specific embodiment, the magnetic oral retractor assembly further comprises at least four lip holders, each including a lip clamp for grasping the patient's lip, each clamp being mounted at a distal end of a separate adjustable arm with a proximal end removably attachable to the support structure, and at least two gripper elements, each of which is mounted on a distal end of a separate mounting arm, the mounting arms having their proximal ends adapted to be removably attached to the support structure for use with opposite sides of the patient's oral cavity, wherein pairs of the lip holders are disposed for use with an associated gripper element to hold the upper and lower lips on opposite sides of the patient's oral cavity.

In another aspect of the invention, a magnetic surgical retractor assembly for securing tissue of a patient undergoing a medical procedure comprises a gripper element and a retractor device for engaging a portion of the tissue, wherein the gripper element and the retractor device each include a magnetic member, at least one of the magnetic members comprising a first magnet, and the other of the magnetic members comprising a second magnet or a non-magnetized magnetically permeable member, the magnetic members being positioned on the gripper element and the retractor device for magnetically coupling the gripper element to the retractor device to enable the gripper element to exert a force on the retractor device to manipulate the tissue.

This aspect of the invention can be embodied in numerous constructions. For example, the retractor device can be adapted for placement within a lumen of a hollow organ or a space within a tissue so that the gripper element interacts magnetically with the retractor device through a wall of the organ or tissue interface. The gripper element can include structure for extending through a body wall of the patient for securing the organ or tissue within the body cavity at a location spaced from the body wall. This aspect of the invention is further applicable to structure in which the gripper element and the retractor device are adapted to interact magnetically with each other through a body wall of the patient. In addition, the retractor device can include a compliant surgical implement such as a laparotomy sponge or surgical towel that has been modified to be either a magnet or magnetically permeable.

BRIEF DESCRIPTION OF THE DRAWINGS

The objects of the invention will be better understood from the detailed description of its preferred embodiments which follows below, when taken in conjunction with the accompanying drawings, in which like numerals refer to like features throughout. The following is a brief identification of the drawing figures used in the accompanying detailed description.

DETAILED DESCRIPTION OF THE PREFERRED EMBODIMENTS

Figure 1:
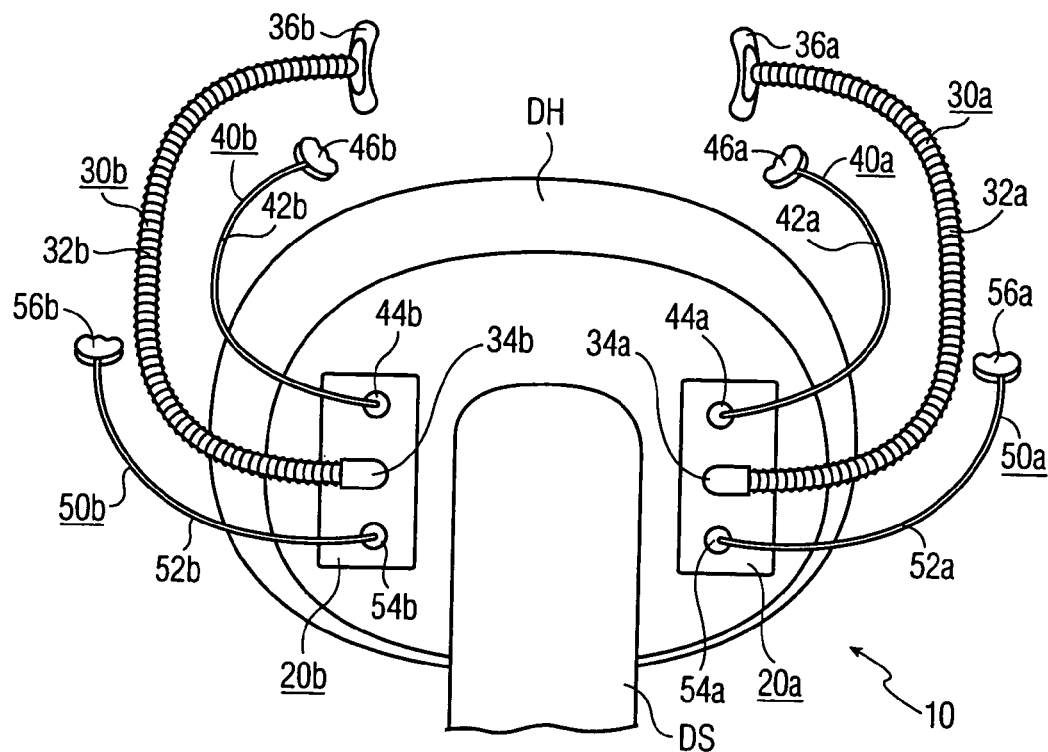
FIG. 1 is a perspective schematic representation of a magnetic oral retractor apparatus in accordance with a first embodiment of the present invention, shown incorporated into the headrest of a dental chair.
Figure 2:
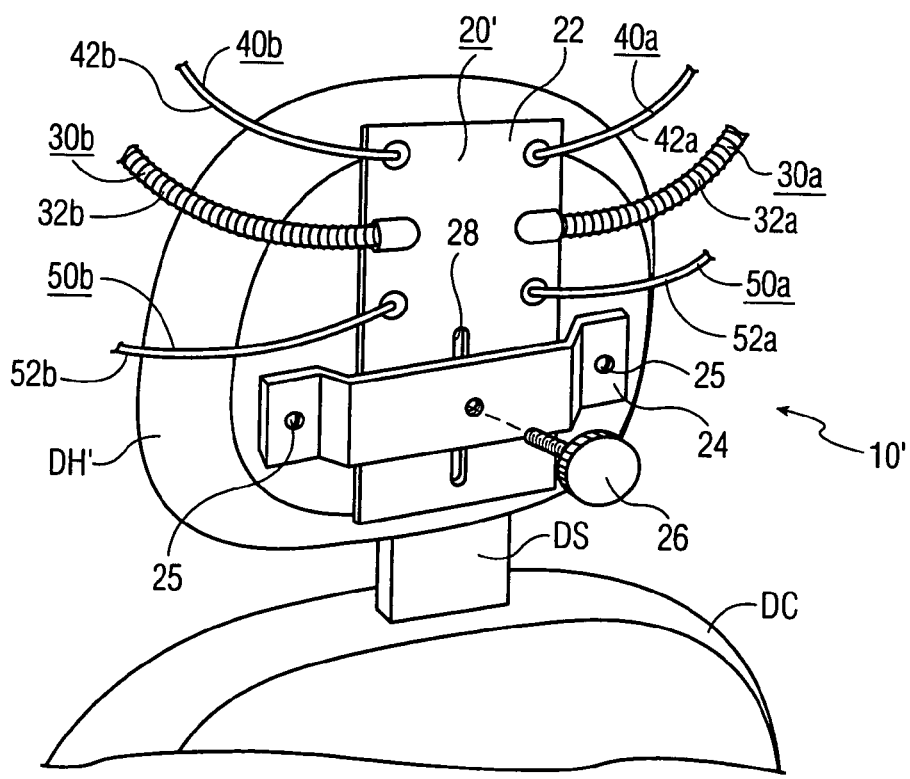
FIG. 2 schematically illustrates a manner of removably mounting a magnetic oral retractor apparatus to the headrest of a dental chair, in accordance with another embodiment of the invention.

FIG. 1 schematically represents a preferred embodiment of a magnetic oral retractor apparatus 10 in accordance with the present invention. The retractor apparatus includes brackets 20a and 20b connected to the headrest DH of an otherwise conventional dental chair. The headrest DH is connected by a conventional adjustable support DS to the dental chair (not shown in FIG. 1). In FIGS. 1 and 2, the retractor apparatus 10 includes two mirror-image left- and right-hand components, the parts of which are indicated by corresponding reference numerals with "a" and "b" suffixes. The following description omits those suffixes, it being understood that reference to a particular feature by number indicates that the description applies to both the right- and left-hand components.

The retractor apparatus 10 includes an external magnetic gripper device 30 with an adjustable arm 32 attached to the bracket 20 by a proximal end connector 34. The connector 34 is constructed to be removably attachable to the bracket 20. The distal end of the arm includes a magnetic gripper element 36 that is described in more detail below in connection with FIG. 3. The apparatus 10 further includes an upper lip holder 40 that includes an adjustable arm 42 removably attached to the bracket 20 by a proximal end connector 44. At its distal end the arm 42 has a spring-loaded clamp 46, that is likewise described in more detail below in connection with FIG. 6. Finally, the apparatus 10 includes a lower lip holder 50 that includes an adjustable arm 52 removably attached to the bracket 20 by a proximal end connector 54. At its distal end the arm 52 has a spring-loaded clamp 56, also described in more detail below in connection with FIG. 6.

FIG. 2 illustrates a retractor apparatus 10' in accordance with another embodiment of the invention that uses a modified mounting bracket 20'. As in FIG. 1, the mounting bracket is attached to the back of a headrest DH' connected to an otherwise conventional dental chair DC by a support DS. The alternate mounting bracket 20' includes a mounting plate 22 to which the arms 32, 42 and 52 are attached as described in connection with FIG. 1. A cross-bar 24 is attached to the back of the headrest DH' by screws 25 or other suitable fasteners. A thumb screw 26 passes through an opening in the cross-bar 24 and enters a slot 28 in the plate 22. A receiving nut (not shown) is slidingly mounted in the slot 28 to accept the thumb screw 26. When the thumb screw is tightened, the plate 22 is firmly secured to the cross bar 24 to fix the bracket in the desired position. With this arrangement, the vertical position of the retractor apparatus can be adjusted in accordance with the patient's physiognomy and/or in accordance with the particular procedure to be carried out.

It should be understood that the mounting arrangements shown in FIGS. 1 and 2 are intended only as being representative of this aspect of the invention. Without departing from the invention, the arms 32, 42 and 52 can be mounted to the dental chair in any manner that accommodates the intended uses of the invention, as described herein. For example, the headrest DH can be manufactured with built-in receptacles that removably mount the proximal ends of the arms 32a, 32b, 42a, 42b, 52a and 52c, thus permitting the dentist or surgeon to attach to the headrest any one or more of the gripper devices and lip holders as needed for a particular procedure, and then to remove them if they are not needed for a different patient. These removable receptacles could be snap-fit connectors that employ a detent mechanism to lock the arms in place while in use, or threaded receptacles for accepting threaded portions on the proximal ends of the arms 32, 42 and 52. In addition, the invention is not limited to mounting the arms to the headrest of a patient chair. They might be carried by a floor stand mounted on casters so that it can be moved into position when a procedure requiring the apparatus is to be performed. They could also be shortened and attached to a handle for manual use by the dentist or assistant to provide additional flexibility in use. Those skilled in the art will be able to envision still other arrangements that fall within the scope of the present invention.

Figure 3:
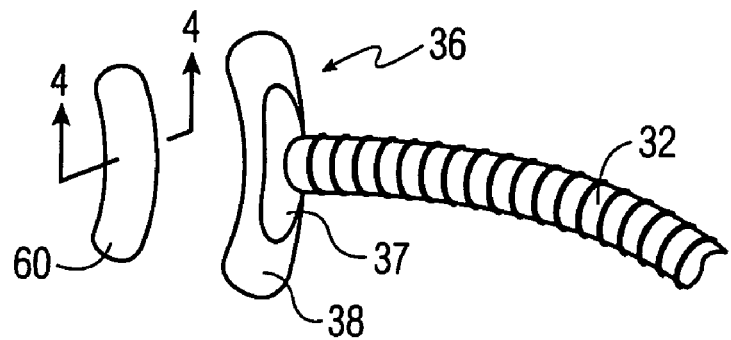
FIG. 3 is a detail view of an external magnetic cheek gripper and intraoral magnetic retractor comprising one preferred embodiment of the present invention.
Figure 4:
FIG. 4 is a sectional view of the intraoral retractor taken along lines 4-4 in FIG. 3.

FIG. 3 is a detail view of the magnetic gripper element 36 shown in FIG. 1. It includes a fixed portion 37 secured to the distal end of the arm 32 and a cheek gripper 38 removably secured to the fixed portion 37. The cheek gripper 38 is a permanent magnet and the fixed portion 37 is a non-magnetized magnetically permeable material. Thus, differently configured cheek grippers 38 can be used with the apparatus. Also illustrated in FIG. 3 is an intraoral retractor element 60, which fits within the patient's oral cavity. The intraoral retractor element 60 is a non-magnetized magnetically permeable material that is attracted to the magnetic cheek gripper 38 in a manner to be described in more detail below in connection with FIG. 6. However, suffice it to say here that the patient's cheek is captured between the intraoral retractor element 60 and the cheek gripper 38, and can be distended by moving the arm 32. Alternatively, or in addition, the patient's head may be oriented in such a way as to provide the desired retraction. FIG. 4, which is a cross section of the intraoral retractor 60 taken along lines 4-4 in FIG. 3, shows how the retractor 60 is gently curved to match the contour of the inside of a patient's cheek, thus making the use of the retractor assembly of the present invention more comfortable than excessive distension of the patient's lips as with conventional oral retractors.

An alternate arrangement uses a magnetized intraoral retractor and a non-magnetized cheek gripper. It is also possible for them both to be magnetized. In that case, they can be magnetized with their magnetic fields oriented such that the intraoral retractor element 60 is positioned relative to the cheek gripper 38 in a predetermined manner when in use. Suitable materials for the permanent magnet component of the invention are neodymium-iron-boron (NeFeB), samarium cobalt (SmCo), and alnico (AlNiCo). NeFeB and SmCo are rare-earth magnets and are preferred because they provide a very strong magnetic force. SmCo is slightly preferred because it is more resistant to corrosion than NeFeB. Alnico can be cast or sintered and therefore can be made into different shapes more readily. Hard ferrite or ceramic magnets, made from a combination of either barium or strontium oxide and iron oxide can also be used. The magnetically permeable material component of the invention can be a material such as cold-rolled steel or an iron-cobalt alloy (with 50% iron-50% cobalt), to name two possible materials known in the prior art.

Figure 5:
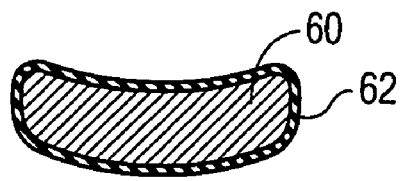
FIG. 5 is a similar sectional view of an alternate embodiment of the intraoral retractor depicted in FIG. 4.

FIG. 5 shows the intraoral retractor 60 having a corrosion-resistant, biocompatible coating 62. This coating may be a compliant material such as silicone rubber to further increase the patient's comfort. In addition, the magnetic cheek gripper may also be coated with a compliant material. Other variations on the construction of the intraoral retractor are also possible. For example, it can be made of a so-called magneto-rheological material, which is fluid-like in the absence of a magnetic field, but becomes highly viscous, approaching a solid, when exposed to a magnetic field. The intraoral retractor could be a hollow body of a compliant material such as silicone rubber, filled with a magento-rheological substance. Such a retractor would mold itself to the patient's cheek before solidifying, thus providing even more comfortable retraction. Suitable materials for this purpose are sold by the Lord Corporation of Cary, N.C. Still other possible constructions of the intraoral retractor include using a gauze material similar to that used now in oral procedures, or medical grade rubber, gel/hydrogel or cloth. Gauze or cloth can be made magnetically permeable by weaving magnetically permeable fibers into the gauze or cloth, or by interspersing magnetically permeable, flexible or malleable strips between layers of gauze or cloth. Magnetically permeable sponges may also be constructed in a similar fashion for use as the retractor 60. In addition, for thicker rolled gauze implements used in dental/oral procedures, a magnet or magnetically permeable element can be contained wholly within the implement. Rubber or gel/hydrogel can be made magnetically permeable by impregnation with granular or powdered forms of the materials mentioned above as being suitable for use in the present invention.

Figure 6:
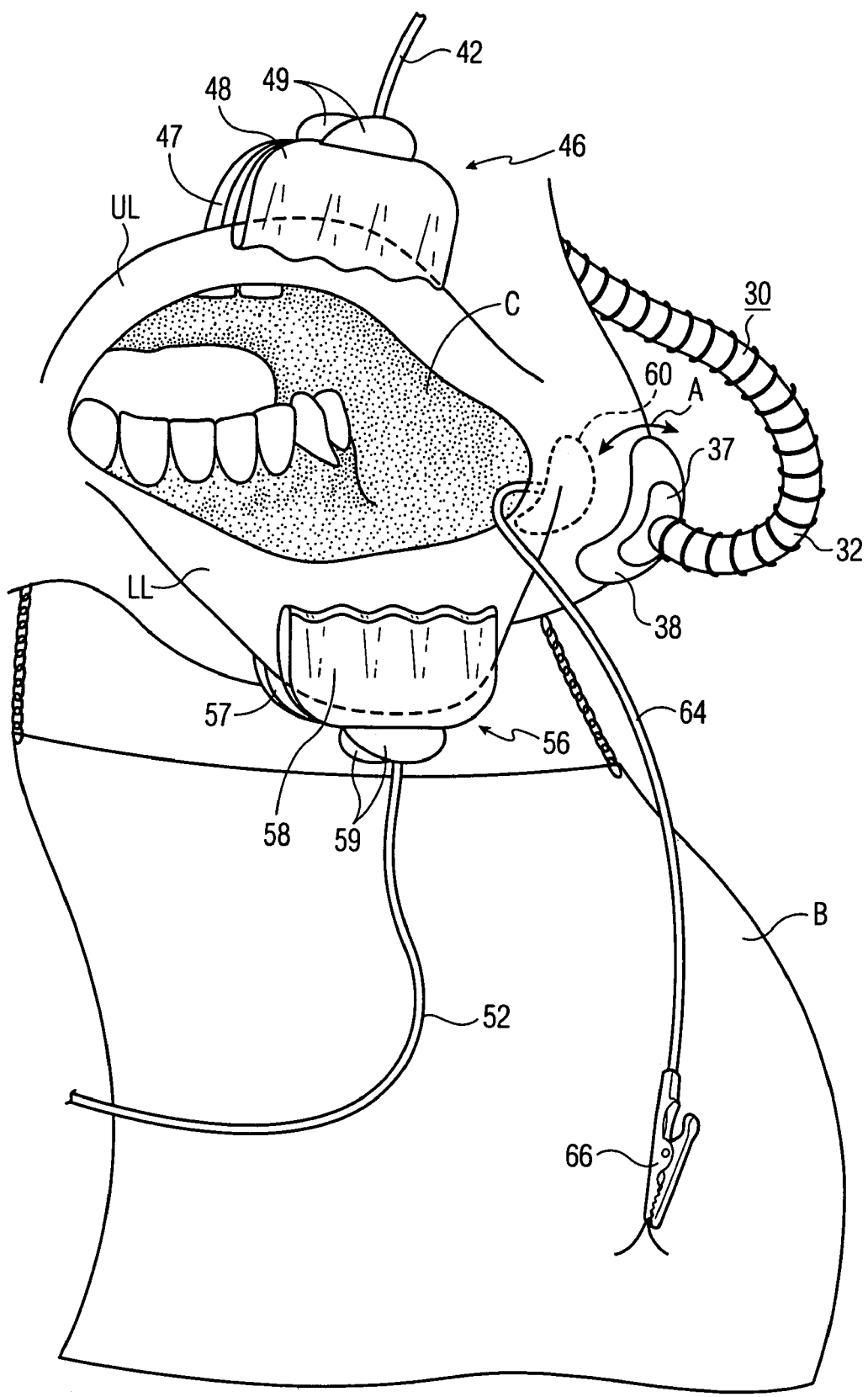
FIG. 6 depicts an embodiment of the magnetic retractor apparatus according to an embodiment of the invention in use to expose a target area within a patient's oral cavity.

FIG. 6 illustrates the apparatus in use to expose a target area within a patient's oral cavity C. The patient is seated in a dental chair with a headrest such as that shown in FIG. 1 or 2 (not seen in FIG. 6). After fitting, the patient with a standard protective bib B, the intraoral retractor 60 is attached to the bib by a monofilament tether 64 terminating in an alligator clip 66 clipped to the bib B. It is preferable to tether the retractor in this manner to prevent the patient from inadvertently swallowing the retractor or choking on it if it somehow becomes separated from the gripper 38 during the procedure. The retractor 60 is placed within the patient's oral cavity C and the arm 32 is brought into position with the gripper element 36 on the outside of the patient's cheek at a location opposing the oral retractor 60. In this manner the patient's cheek is firmly but gently captured between the retractor 60 and the magnetic cheek gripper 38. The arm 32 is of a construction that resists movement, but can be placed in a desired position by exerting force thereon. In the depicted embodiment, the arm 32 is segmented with adjoining segments in frictional engagement, in the manner of a supporting arm of a conventional gooseneck lamp. The arm can also be manipulated to rotate the gripper element 36 in the direction of the arrow A to cause it to assume a position that will provide maximum contact area with the patient's cheek, and thereby form a stronger connection with the retractor 60 and minimize patient discomfort. It will be immediately apparent to those skilled in the art that the arm 32 can be of other constructions, as long as it is sufficiently flexible to be moved into a desired position manually, and will then maintain that position until moved again.

As shown in FIG. 6, the gripper device 30 is moved to a position where the patient's cheek is distended away from the buccal surfaces of the patient's teeth and gums. Once the cheek is retracted, the lip holders included in this embodiment of the invention can be used to hold the patient's lips out of the way. The upper lip holder clamp 46 includes an outer member 47 hinged to an inner member 48, and the members are urged together by a spring (not shown). The user squeezes the handles 49 together to spread them apart and to fit them over the patient's upper lip UL as shown, and when the handles are released the spring is just strong enough to hold the patient's lip between the members. The adjustable arm 42 is rigid enough to hold the patient's lip in the folded back position shown in FIG. 6. Typically, a single wire of a suitable material and thickness Swill suffice for this purpose. The lower lip holder 56 is constructed generally the same manner as the upper lip holder, with like parts having corresponding "50" reference numerals corresponding to the "40" reference numerals used to describe the upper lip holder. The lower lip holder folds back the patient's lower lip LL in the manner discussed above in connection with the upper lip holder. The clamps 46 and 56 are made of a suitable plastic material and have gently serrated edges for more securely holding the lips. The inner surfaces of the members can have a positive profile relief to prevent slippage, and they can also incorporate a compliant material to be more comfortable to the patient.

It can be seen from FIG. 6, which is based on a photograph of a prototype of the present invention in use, that the present invention provides a large space in the patient's oral cavity, and thereby enables unobstructed access to the buccal surfaces of the patient's teeth and gums. The present invention takes advantage of the fact that the cheeks are more distensible than the lips, and thus retracts the cheeks, rather than attempting to provide space within an oral cavity by trying to pull back the patient's lips. Once the cheek is distended, it is unnecessary to forcibly retract the lips. They only need be gently folded out of the way, thus making the retraction, which is a necessary part of the procedure, more comfortable for the patient. This is especially advantageous for lengthy procedures. In addition, there are no retractor elements traversing the patient's mouth, as with some prior art retractors, thus providing unhampered access to the target area.

FIG. 6 illustrates a procedure in which only one side of the patient's oral cavity is retracted. It is apparent from the figure that this application of the invention uses only one of the "a" or "b" components of the retractor apparatus 10 shown in FIG. 1. In that case, the other component would be moved out of the way if it were permanently attached to the headrest DH. If the "a" and "b" components are removably attached to the dental chair, then only those components necessary for the procedure would be mounted to the headrest prior to preparing the patient, and the remaining parts would be omitted. Likewise, if the apparatus were on a movable stand, or mounted in some other manner, the components, would be used as needed for any given procedure.

Figure 7:
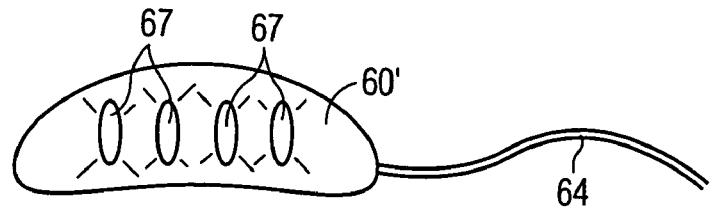
FIG. 7 is a plan view of another alternate embodiment of FIG. 4's intraoral retractor, capable of illuminating a target area of a patient.
Figure 8:
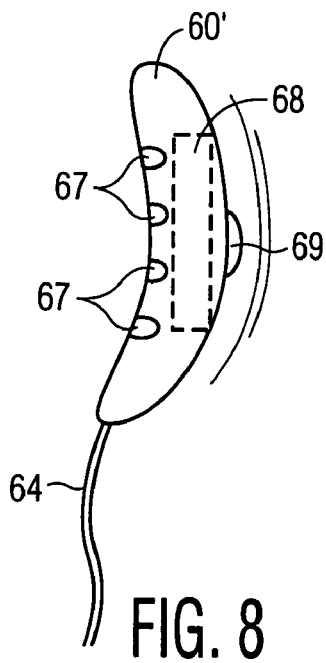
FIG. 8 is a top view of the intraoral retractor shown in FIG. 7.

Many other variations of the parts of the invention described above are possible. FIGS. 7 and 8 depict an alternate embodiment 60' of the intraoral cheek retractors shown in FIGS. 4 and 5. FIG. 7 is a plan view of the retractor 60', showing a series of LEDs 67 on the surface of the retractor that faces the target area when the retractor is in place (FIG. 6). The LEDs are powered by a battery 68 in the retractor, as seen in the side view of FIG. 8. The battery 68 is connected to the LEDs 67 through an electrical circuit (not shown) within the retractor 60'. The circuit includes a pressure switch 69 that activates the LEDs when the retractor is pressed against the patient's cheek by the magnetic force between the cheek gripper magnet 38 and the retractor 60'. Alternatively, the line 64 connected to the retractor can be a power cord that supplies power to the LEDs. In addition, LEDs that emit light in particular wavelength ranges may be used if the procedure involves curable or light-activated materials, such as those used in composite bonding or cementation procedures. In another construction, the surface of the retractor 60 facing the patient's teeth (see FIG. 6) can be mirrored, thus affording the dentist or oral surgeon with a view of the procedure target area.

In another alternate embodiment, the cheek gripper magnet 38 can be an electromagnet, controllable by the dentist or oral surgeon through a foot pedal or other control (not shown). Use of an electromagnet would facilitate placement of the retractor/gripper when in use. That is, it may be desirable in some instances to use trial and error to locate the intraoral retractor 60 in the most advantageous position for particular procedures. In that case, it will be easier to locate the intraoral retractor 60 before activating the gripper magnet 38. If the practitioner then desires to try a different position, that can be done more readily if the magnetic force is released.

Figure 9:
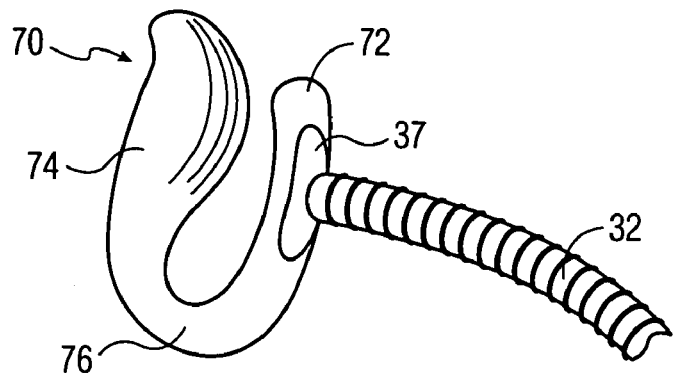
FIG. 9 depicts a magnetically coupled retractor in accordance with another embodiment of the invention.

FIG. 9 illustrates yet another application of the inventive principle of employing magnetic force to provide retraction of tissues for surgical/dental procedures. The fixed portion 37 on the arm 32 can be used to hold a conventional retractor blade 70, which has a handle portion 72 and a blade 74 connected by a U-shaped contact portion 76. The handle portion is configured to fit on the fixed portion 37, replacing the magnetic cheek gripper 38 of the above-described embodiment. In this application, the retractor blade 70 can either be a magnet (like the cheek gripper), or, more preferably, the fixed portion 37 is a magnet and the retractor blade is a non-magnetized, magnetically permeable material. Any suitable prior art retractor blade that engages an edge of the patient's mouth can be used with this embodiment of the invention. Suitable retractor blades are shown in U.S. Pat. Nos. 4,971,557, 5,115,799, and 5,730,597, which are incorporated herein by reference. This embodiment of the invention will be useful when it is desirable to retract the patient's lips, or periphery of another body cavity or other tissue, to provide access to the target area for the procedure. Like other embodiments described, this embodiment has the advantage of eliminating the need to have someone manually maintain the retraction force on the retractor.

Figure 10:
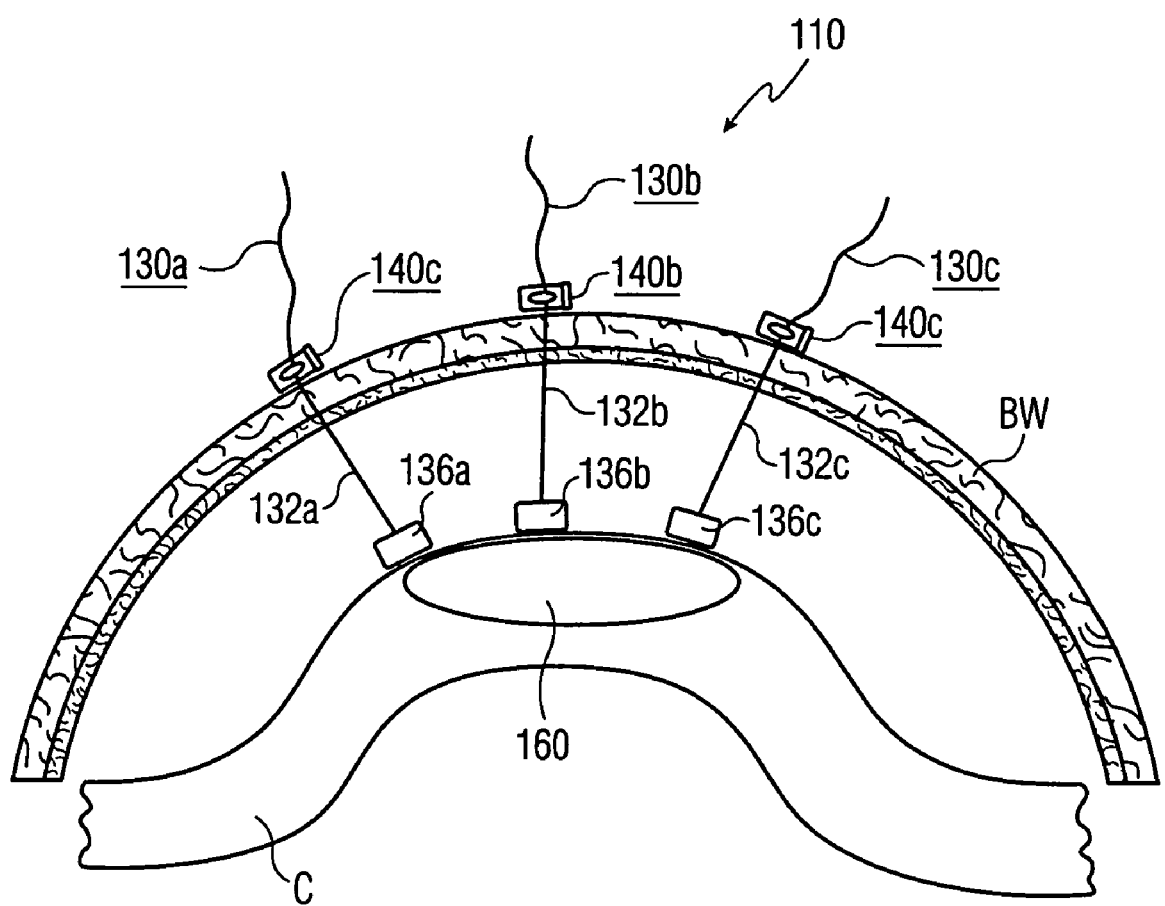
FIG. 10 depicts a magnetic surgical retractor assembly used to secure patient tissue in place during a surgical procedure.

FIG. 10 illustrates another aspect of the invention, for holding tissue in place during a surgical procedure. (Unless otherwise indicated explicitly or by context, "tissue" is meant to refer to any body tissue, including organs or other body parts.) The embodiment in FIG. 10 is particularly adapted to holding a luminous organ, such as the colon C, out of the way during a laparoscopic procedure on nearby tissue (not shown), or for suspending it for devascularization and subsequent excision. FIG. 10 depicts a retractor device 110 comprising three gripper devices 130a, 130b and 130c for purposes of illustrating the principles of the present embodiment, but any number can be used in accordance with the requirements of the particular procedure being performed. (As before, the remainder of this description omits the "a," "b" and "c" suffixes, it being understood that reference to a particular feature by number indicates that the description applies to the corresponding gripper device, as illustrated in FIG. 10.) Each gripper device 130 includes a cord 132 that has a magnetic gripper element 136 at its distal end. Each gripper device also includes a cord clamp 140 that tightly clamps around the cord 132 outside the body wall BW. The retractor device 110 also includes an intraluminal retractor 160 introduced into the colon C. As in the previous embodiment, the gripper elements 136 can be magnets while intraluminal retractor 160 is a non-magnetized magnetically permeable member, or both can be magnets. The materials discussed above as suitable for the gripper element 36 and the retractor 60 can also be used for the gripper element 136 and the retractor 160.

In operation, the intraluminal retractor 160 is inserted into the colon C transanally or dropped off endoscopically, for placement in the area of the colon that is to be retracted or excised during a laparoscopic procedure. The gripper elements 136 are introduced through standard laparoscopic trocars (not shown) in the body wall BW and manipulated laparoscopically into place on the outside surface of the colon C adjacent the retractor 160. This captures the colon wall between the gripper elements and the retractor. A conventional small hook probe (for example, one with a diameter of less than 3 mm) having a sharp point can then be passed through the body wall to retrieve the cords and bring them extracorporally so they can be introduced into the clamps 140. The use of hook probes of this type does not require trocars because of the small size of the probes. The cords 132 can then be drawn through the clamps 140, which are located to provide a suitable angle of retraction, until the colon is in the desired location, and the clamps, acting through the cords, hold the colon in place during the procedure. This embodiment, with its inherent adjustability of the cords 132 is particularly advantageous when the tissue or organ to be manipulated cannot reach the body wall BW. This embodiment can be used with any luminous organ or across any tissue interface, whether it exists anatomically or is created by the surgeon specifically to manipulate the tissue in the desired fashion. The distance between the body wall and the retracted tissue can be adjusted by changing the length of the cords 132 using a laparoscopic instrument or the hook probes.

In another embodiment of the invention, the retraction arrangement described above employing cords 132 and extracorporeal clamps 140 can be used without magnetic members to secure an internal organ or other tissue in a location spaced from a body wall. In that case, the gripper elements would comprise tissue clamps that lock on the tissue and are deployed from a laparoscopic instrument or applied by hand during a hand-assisted laparoscopic (HAL) procedure. A non-magnetic application of this aspect of the invention may be appropriate for anatomical locations that do not lend themselves to the use of an intraluminal retractor (such as the retractor 160), or with tissues that cannot be manipulated to provide a space for such a retractor. The cords may be adjusted as described above in connection with the magnetic embodiment of this aspect of the invention.

Figure 11:
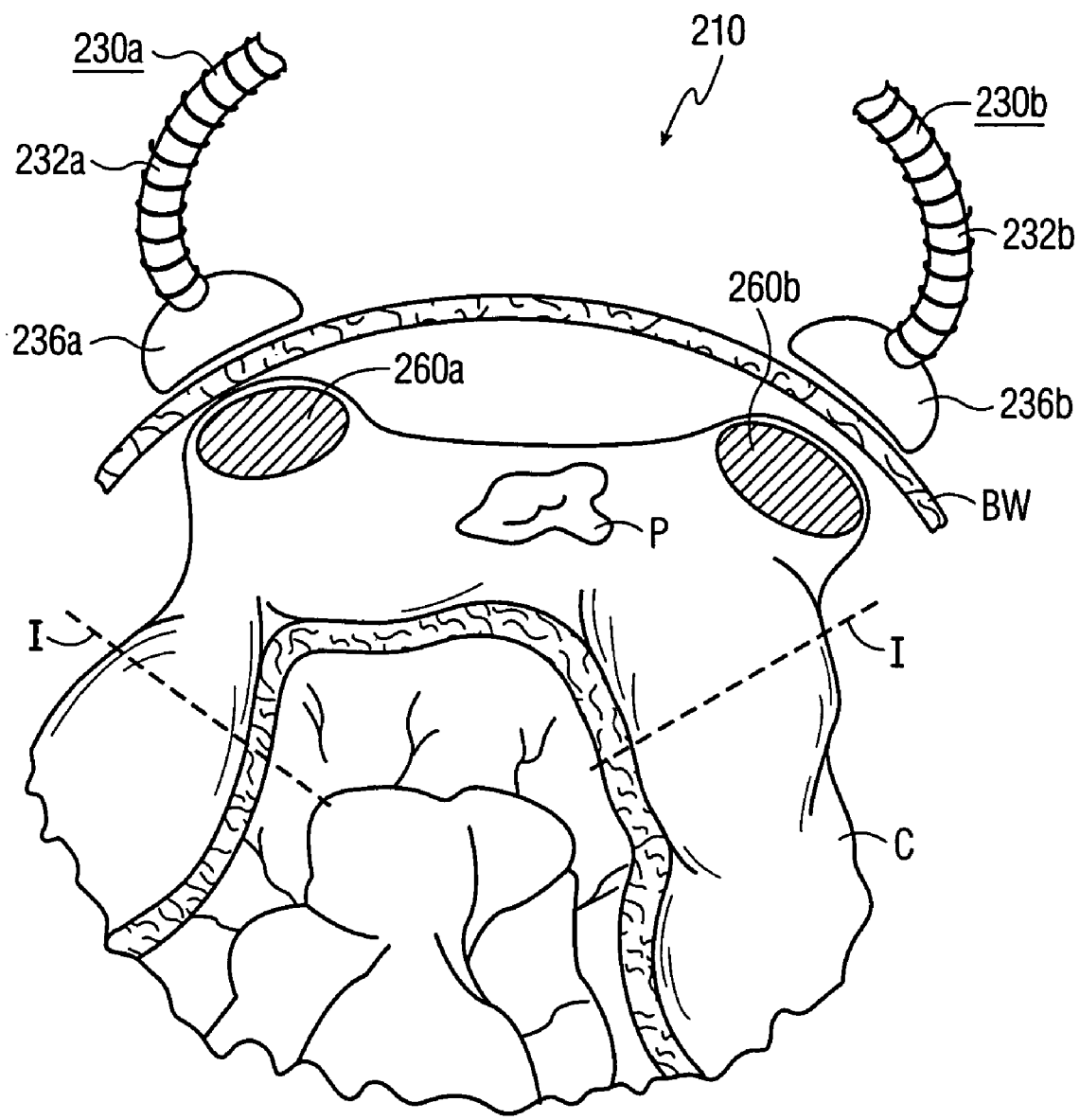
FIG. 11 depicts an alternate embodiment of a magnetic surgical retractor assembly used to secure patient tissue in place during a surgical procedure.

FIG. 11 illustrates another embodiment of the invention useful in non-dental surgical applications. In this embodiment, a retractor device 210 includes grippers 230a and 230b, and corresponding intraluminal retractors 260a and 260b. This device also has great utility in laparoscopic procedures, an example being the resection of a colon C along incisions I to remove a section of the colon containing a pathology such as a polyp P. In this embodiment, each gripper 230 includes an arm 232 having at its distal end a gripper element 236. Meanwhile, the retractors 260 are introduced transanally into position ahead and behind the polyp P, as shown in FIG. 11. As before, the gripper elements 236 can be magnets while the intraluminal retractors 260 are a non-magnetized magnetically permeable member, or all of them can be magnets. Thus, when the gripper elements are proximate to the retractors, they interact magnetically with each other through the body wall BW and the wall of the colon C therebetween to secure the colon in the desired position for resection. It will be appreciated that the gripper elements and retractors can hold internal tissues in place even if spaced apart, as long as they are sufficiently proximate to interact magnetically and secure the tissue in place. It should also be appreciated that the retractors 260 can be held in place by a single gripper element.

The retractors 160 and 260 can be constructed as discussed above in connection with the dental/oral retractor device 60. For example, the retractors 160 and 260 can comprise a hollow body of a compliant material such as silicone rubber, filled with a magnetically permeable gel or a magneto-rheological substance. Nor is this aspect of the invention limited to use in procedures involving the colon; it will be appreciated that the same operational principles apply to any luminous organ, such as the stomach, small intestine, urinary bladder, etc. The invention can be used as illustrated in FIG. 11 to secure the organ during a procedure on the organ itself, but it is also capable of securing the organ in place, and temporarily out of the way, during procedures on adjoining tissues. Further, other aspects of the invention described above with reference to the oral retractor aspect of the invention are likewise applicable to the non-dental surgical aspects of the invention. This includes the use of LEDs for illumination and/or curing, electromagnets, compliant coatings, and the magnetic and magnetically permeable materials mentioned in connection with the oral retractor aspects of the invention.

Figure 12:
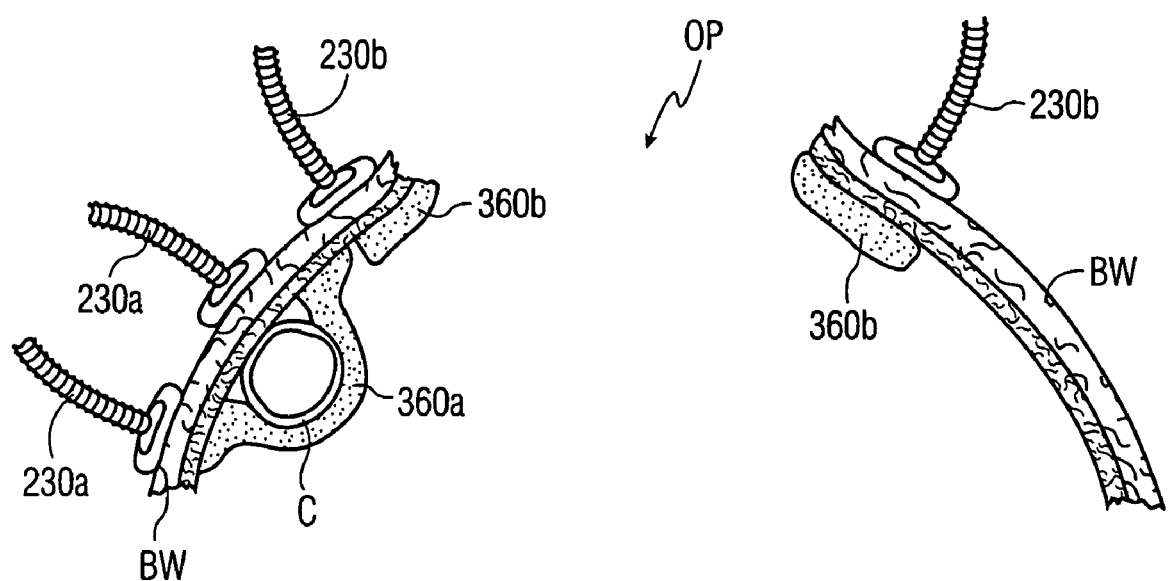
FIG. 12 depicts another embodiment of a magnetic surgical retractor assembly for securing patient tissue in place or distending an opening in a patient's body wall during a surgical procedure.

FIG. 12 illustrates other surgical applications of the invention. A conventional laparotomy sponge, such as the cloth-wrapped DISARP single patient use abdominal sponge sold by Unomedical A/S, can be modified to make it magnetically permeable for use in the present invention. One modification with particular utility involves including a magnet or magnetically permeable material within the sponge. As discussed above, this type of sponge normally will not maintain a desired position throughout a surgical procedure, often requiring adjustment during the procedure. By incorporating a magnet member (a magnet or magnetically permeable element) in the sponge, its position can be maintained through magnetic interaction with a cooperating magnetic member on the opposite side of the patient's body wall. Other conventional surgical implements, such as surgical towels, can be modified to be magnetic or magnetically permeable for use as retractors in the present invention. For example, the necessary modifications may be made in the manner discussed above for making gauze or cloth magnetically permeable.

The thus-modified sponge can then be used as a retractor device, as shown in FIG. 12. In one embodiment, the sponge retractor device 360a is placed so as to pack off the tissues or an organ, such as the colon C, from the target surgical area. The sponge is held in place through interaction through the body wall by magnetic grippers 230a. The sponge or other retractor element need not contact the body wall BW as shown in FIG. 12. For example, in some applications the sponge may be held in position at a distance from the body wall by the magnetic attraction of the magnetic members in the sponge and grippers. Another application involves using a laparotomy sponges 360b (or other magnetic or magnetically permeable elements) and magnetic grippers 230b attached to an external structure (not shown), in the place of conventional mechanical retraction devices during a surgical procedure. By exerting a force on the grippers 230b, the opening OP in the body wall BW, or other tissue plane depending on the area where the invention is being used, is distended for access to the tissue undergoing the surgical procedure. This will reduce the amount of trauma to the patient during the surgical procedure by allowing for better load distribution of forces on the tissues, hasten healing, and reduce post-operative pain. Prior mechanical retractors for body wall retraction, or retraction of other tissue planes, typically engage the tissue at a very focal area, rather that distributing the retraction forces over a wider area.

Another aspect of the invention involves retractor devices filled with magneto-rheological material as discussed above, for applications other than magnetically securing tissue across a tissue boundary as described above. For example, a retractor device in accordance with this aspect of the invention can be a hollow body of compliant material filled with a magneto-rheological substance that is fluid-like in the absence of a magnetic filed, but becomes highly viscous when exposed to a magnetic field. An example of such a retractor device is described above in connection with FIG. 5, but it could assume any configuration suitable for the specific tissue being retracted, including configurations used in the prior art. A retractor device in accordance with this aspect of the invention is particularly adapted for retraction of delicate tissues such as those found in the brain, since it is pliant enough to mold to the tissue, and then can be made sufficiently rigid to effect retraction by the application of a magnetic field, preferably by activation of an electromagnet. The magneto-rheological material can, for example, be contained within a highly compliant vessel of silicone or other acceptable biomaterial, perhaps with a soft coating (such as a hydrogel). The vessel would be placed like a sleeve over the blade of an otherwise conventionally configured retractor device, but which has been modified to be an electromagnet. The electromagnetic retractor blade would enable the rheological sleeve to conform precisely to the tissue before application of the magnetic field, application of which would cause the fluid in the sleeve to be converted to a semi-solid as discussed previously. The exact mechanical properties, such as yield strength, of the semi-solid can be selected depending the tissue characteristics and needs of the surgeon. Retractor devices in accordance with this aspect of the invention can also include other features described above, such as incorporating illumination devices.

Those skilled in the art will readily recognize that the principles underlying the present invention has a wide variety of applications. In that connection, only selected preferred embodiments of the invention have been depicted and described, and it will be understood that various changes and modifications can be made other than those specifically mentioned above without departing from the spirit and scope of the invention, which is defined solely by the claims that follow.

What is claimed is:

1. A method for holding a hollow internal organ in a desired location during a medical procedure, the method comprising:
    providing at least one retractor device and at least one gripper element, wherein said gripper element and said retractor device each include a magnetic member, at least one of said magnetic members comprising a first magnet, and the other of said magnetic members comprising a second magnet or a non-magnetized magnetically permeable member;
    placing said retractor device into a lumen of the organ of a patient undergoing the medical procedure without attaching said retractor device directly to the organ;
    locating said gripper element outside a body cavity of the patient;
    bringing said magnetic members of said gripper element and said retractor device into proximity, with a wall of the hollow organ and a body wall of the patient captured between said retractor device and said gripper element; and
    holding said gripper element at a location that exerts a force on the hollow internal organ to secure it in the desired location.

2. The method of claim 1, further comprising placing said retractor device into the lumen of the organ of the patient through a body orifice.

3. The method of claim 1, further comprising holding said gripper element using a movable arm.

4. The method of claim 1, wherein only one of said magnetic members is a magnet.

5. The method of claim 1, wherein said first and/or said second magnets are permanent magnets.

6. The method of claim 1, wherein said gripper element is a magnet and said retractor device consists essentially of a compliant hollow member having magneto-rheological material therein that is fluid-like in the absence of a magnetic field and highly viscous when in the presence of a magnetic field.

7. The method of claim 1, wherein said retractor device is a compliant surgical implement.

8. The method of claim 7, wherein said compliant surgical implement includes at least one of a magnet and magnetically permeable material.

9. The method of claim 7, wherein said gripper element is a magnet and said surgical implement comprises at least one of (i) a gauze including a magnetically permeable material, (ii) a cloth including a magnetically permeable material, (iii) a laminated cloth with layers of magnetically permeable material, (iv) rubber, gel or hydrogel including magnetically permeable material, and (v) a surgical sponge including magnetically permeable material.

10. The method of claim 1, wherein said gripper element is a magnet and said retractor device consists essentially of a magnetically permeable material coated with a compliant, corrosion-resistant biocompatible material.

11. The method of claim 1, further comprising:
    providing at least two said gripper elements and two said retractor devices;
    placing each said retractor device into the lumen of the organ at spaced apart locations without attaching either said retractor device directly to the organ;
    bringing said magnetic member of each said gripper element and a respective said retractor device into proximity, with a wall of the hollow organ and a body wall of the patient captured between said retractor device and said respective gripper element;
    holding said gripper elements at locations that secure the organ in place with a portion thereof to be removed accessible for a surgical operation; and
    removing the portion from the organ after the organ is secured in place.

12. A method for holding in a desired location during a medical procedure a hollow internal organ disposed within a body cavity of a patient, the method comprising:
    providing at least one retractor device and at least one gripper element, wherein said gripper element and said retractor device each include a magnetic member, at least one of said magnetic members comprising a first magnet, and the other of said magnetic members comprising a second magnet or a non-magnetized magnetically permeable member;
    placing said retractor device into a lumen of the organ of a patient undergoing the medical procedure without attaching said retractor device directly to the organ;
    locating said gripper element inside the body cavity of the patient and outside the organ;
    bringing said magnetic members of said gripper element and said retractor device into proximity, with a wall of the hollow organ captured between said retractor device and said gripper element;
    locating externally of the patient a proximal portion of a securing member having a distal portion attached to said gripper element; and anchoring said proximal portion of said securing member at a location that exerts a force on said gripper element to secure the hollow internal organ at the desired location.

13. The method of claim 12, further comprising introducing said gripper element inside the body cavity of the patient through a trocar.

14. The method of claim 12, further comprising placing said retractor device into the lumen of the organ of the patient through a body orifice.

15. The method of claim 12, wherein said securing member is a cord, the method further comprising retrieving said proximal portion of said cord from inside the body cavity of the patient using a hook probe inserted through a body wall of the patient without using a trocar.

16. The method of claim 12, wherein only one of said magnetic members is a magnet.

17. The method of claim 12, wherein said first and/or said second magnets are permanent magnets.

18. The method of claim 12, wherein said gripper element is a magnet and said retractor device consists essentially of a compliant hollow member having magneto-rheological material therein that is fluid-like in the absence of a magnetic field and highly viscous when in the presence of a magnetic field.

19. The method of claim 12, wherein said retractor device is a compliant surgical implement.

20. The method of claim 19, wherein said compliant surgical implement includes at least one of a magnet and magnetically permeable material.

21. The method of claim 19, wherein said gripper element is a magnet and said surgical implement comprises at least one of (i) a gauze including a magnetically permeable material, (ii) a cloth including a magnetically permeable material, (iii) a laminated cloth with layers of magnetically permeable material, (iv) rubber, gel or hydrogel including magnetically permeable material, and (v) a surgical sponge including magnetically permeable material.

22. The method of claim 12, wherein gripper element is a magnet and said retractor device consists essentially of a magnetically permeable material coated with a compliant, corrosion-resistant biocompatible material.

23. The method of claim 12, further comprising:
providing a plurality of said gripper elements;
locating said plurality of gripper elements inside the body cavity of the patient and bringing said magnetic member of each said gripper element into proximity with said magnetic member of said retractor device with a wall of the hollow organ captured between said retractor device and said gripper elements;
locating externally of the patient a proximal portion of each of a plurality of said securing members, each securing member having a distal portion attached to a respective said gripper element;
anchoring said proximal portions of said securing members at locations that secure the hollow internal organ at the desired location to provide room for a surgical procedure inside the body cavity of the patient; and
performing the surgical procedure after the organ is secured at the desired location.

24. The method of claim 23, wherein said plurality of said gripper elements are brought into proximity with one said retractor device comprising a single magnetic member.

* * * * *